(12) United States Patent
Nemoto

(10) Patent No.: US 6,679,768 B2
(45) Date of Patent: Jan. 20, 2004

(54) ORBITAL DENTAL POLISHING DEVICE

(76) Inventor: Timothy Tamio Nemoto, #3 - 5575 Oak Street, Vancouver, British Columbia (CA), V6M 2V5

( * ) Notice: Subject to any disclaimer, the term of this patent is extended or adjusted under 35 U.S.C. 154(b) by 0 days.

(21) Appl. No.: 09/920,046

(22) Filed: Aug. 1, 2001

(65) Prior Publication Data

US 2003/0027511 A1 Feb. 6, 2003

(51) Int. Cl.[7] .............................................. B24B 23/00
(52) U.S. Cl. ........................ 451/357; 451/527; 451/913
(58) Field of Search ................................ 451/357, 522, 451/163, 162, 527, 532, 913; 15/167.1, 167.2

(56) References Cited

U.S. PATENT DOCUMENTS

| 2,859,627 | A | | 11/1958 | Gallop ............................ 74/16 |
| 3,902,279 | A | | 9/1975 | Lookadoo |
| 3,961,521 | A | | 6/1976 | Bailey et al. |
| 4,123,845 | A | | 11/1978 | Fattaleh |
| 4,733,432 | A | * | 3/1988 | Novoselsky ................. 15/340 |
| 4,772,201 | A | | 9/1988 | Johnsen et al. |
| 4,845,795 | A | * | 7/1989 | Crawford et al. ............ 15/22 R |
| 5,076,202 | A | * | 12/1991 | Falls ............................ 118/669 |
| 5,088,145 | A | * | 2/1992 | Whitefield ................... 15/22.1 |
| 5,660,546 | A | | 8/1997 | Shafer |
| 5,915,966 | A | | 6/1999 | Miller |
| 5,964,006 | A | * | 10/1999 | Holmes et al. ............... 15/180 |
| 6,132,421 | A | * | 10/2000 | Clapham ........................ 606/4 |
| 6,171,175 | B1 | | 1/2001 | Shaikh et al. ................. 451/28 |

FOREIGN PATENT DOCUMENTS

| DE | 19510900 | 2/1996 |
| EP | 0535391 | 4/1993 |

OTHER PUBLICATIONS

International Search Report, International Application No. PCT/CA 02/01202, filed Jul. 31, 2002; Timothy Tamio Nemoto, pp. 1–4.

English–language Abstract for JP 58 149, 165, published Feb. 26, 1982.

* cited by examiner

Primary Examiner—Eileen P. Morgan
(74) Attorney, Agent, or Firm—Baker Botts L.L.P.

(57) ABSTRACT

Currently dental laboratories use a lathe for the polishing of the dental crown. Such lathes use a polishing disc brush mounted on a rotating shaft and which generally cannot polish the deeper parts of the surface of the appliance without wearing down the surrounding anatomy. The present device provides a brush which uses an orbital motoin to thereby better preserve the anatomy of the crown.

12 Claims, 5 Drawing Sheets

ORBITAL DENTAL POLISHING DEVICE

TECHNICAL FIELD

The invention relates to the field of tools for polishing crowns, bridges, dental appliances such as dentures and the like, or jewellery, and more particularly a device which polishes crowns, bridges, dental appliances such as dentures and the like, or jewellery, using an orbital motion.

BACKGROUND

Currently dental laboratories prepare crowns, bridges and dental appliances such as dentures. After a crown is cast out of gold alloy or porcelain, it is necessary to polish the upper surface of the crown. The upper or functional surface of the crown, like a natural tooth, has a complex convoluted shape or anatomy consisting of convex ridges, concave grooves and a deep central pit. The combination of deep anatomy and projecting ridges is important for the proper functioning of the tooth, and places less stress on the tooth root.

Currently dental laboratories use a lathe for the polishing of the crown or dental appliance. Such lathes use a polishing disc brush made of rigid brushes which is mounted on a rotating shaft. The edge of the rotating disc contacts the surface of the crown. Since the radius of the disc is necessarily too great for the disc to enter the pit, it is generally not possible to polish the depth of the pit without wearing down the surrounding anatomy. Similarly the disc cannot reach all parts of the grooves and ridges without wearing down the anatomy of the crown, which is undesirable. There is therefore a need for a device for polishing crowns, bridges or dental appliances which preserves the anatomy of the crown.

SUMMARY OF THE INVENTION

The present invention provides a device for polishing a workpiece having a convoluted surface comprising: a brush-supporting member; an electric motor for imparting an orbital motion to the brush-supporting member; and a polishing brush comprising a curved working surface mounted on the brush-supporting member. According to one aspect, the brush has a hemispherical face. The hemispherical face preferably faces vertically downwardly. The device may have a horizontal base, and may comprise a vertical motor support. The motor may be mounted within a motor housing on said vertical motor support. Preferably the brush-supporting plate extends downwardly from said motor housing and the device preferably has a plurality of brushes mounted on said brush-supporting plate.

BRIEF DESCRIPTION OF THE DRAWINGS

In drawings which illustrate a preferred embodiment of the invention.

DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive, sense.

Figure 1:
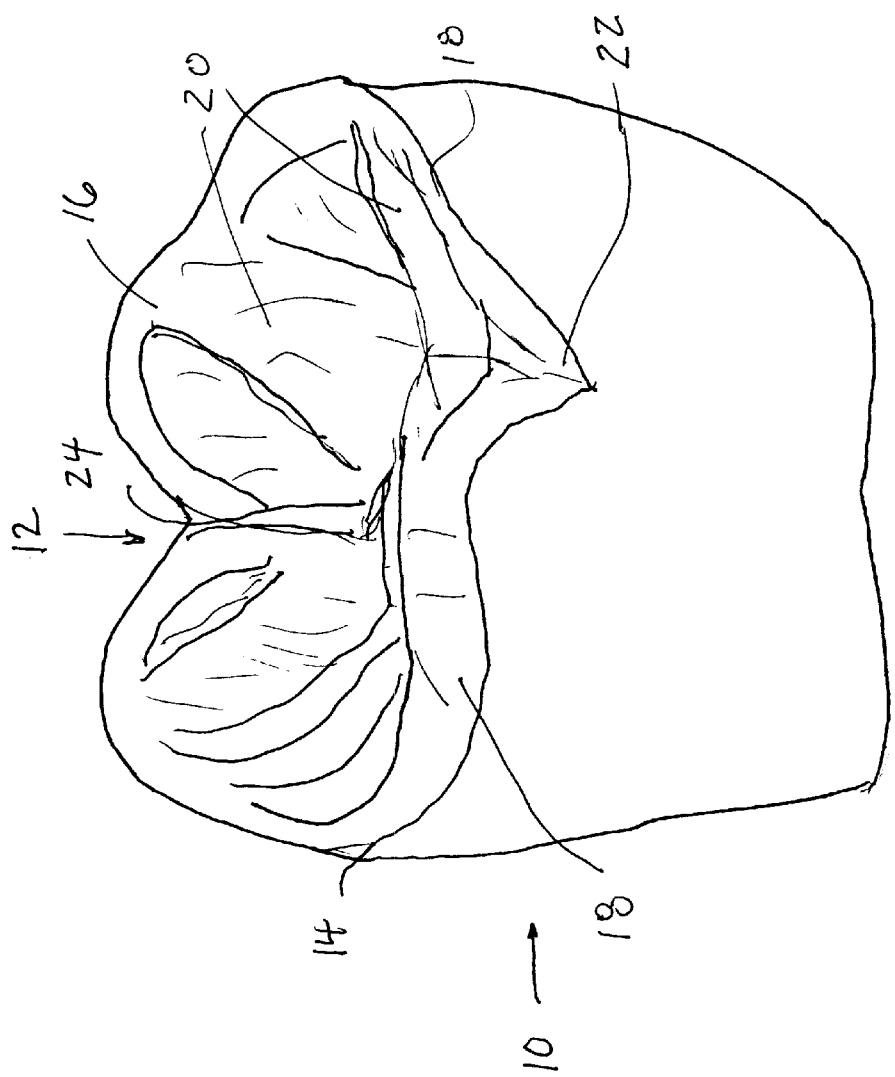
FIG. 1 is a perspective view of the surface of a crown.
Figure 2:
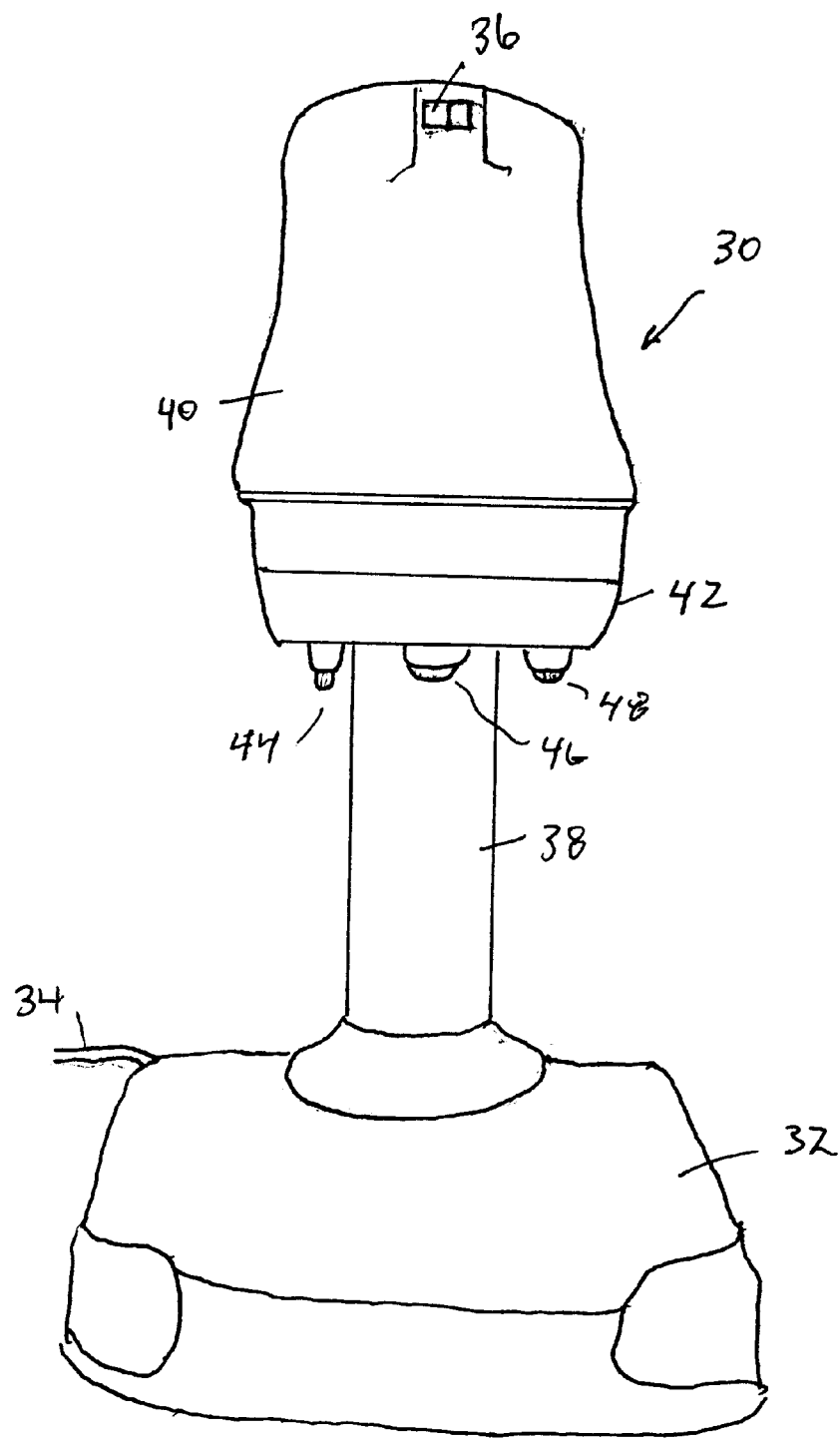
FIG. 2 is a perspective view of the polishing device according to the invention.
Figure 3:
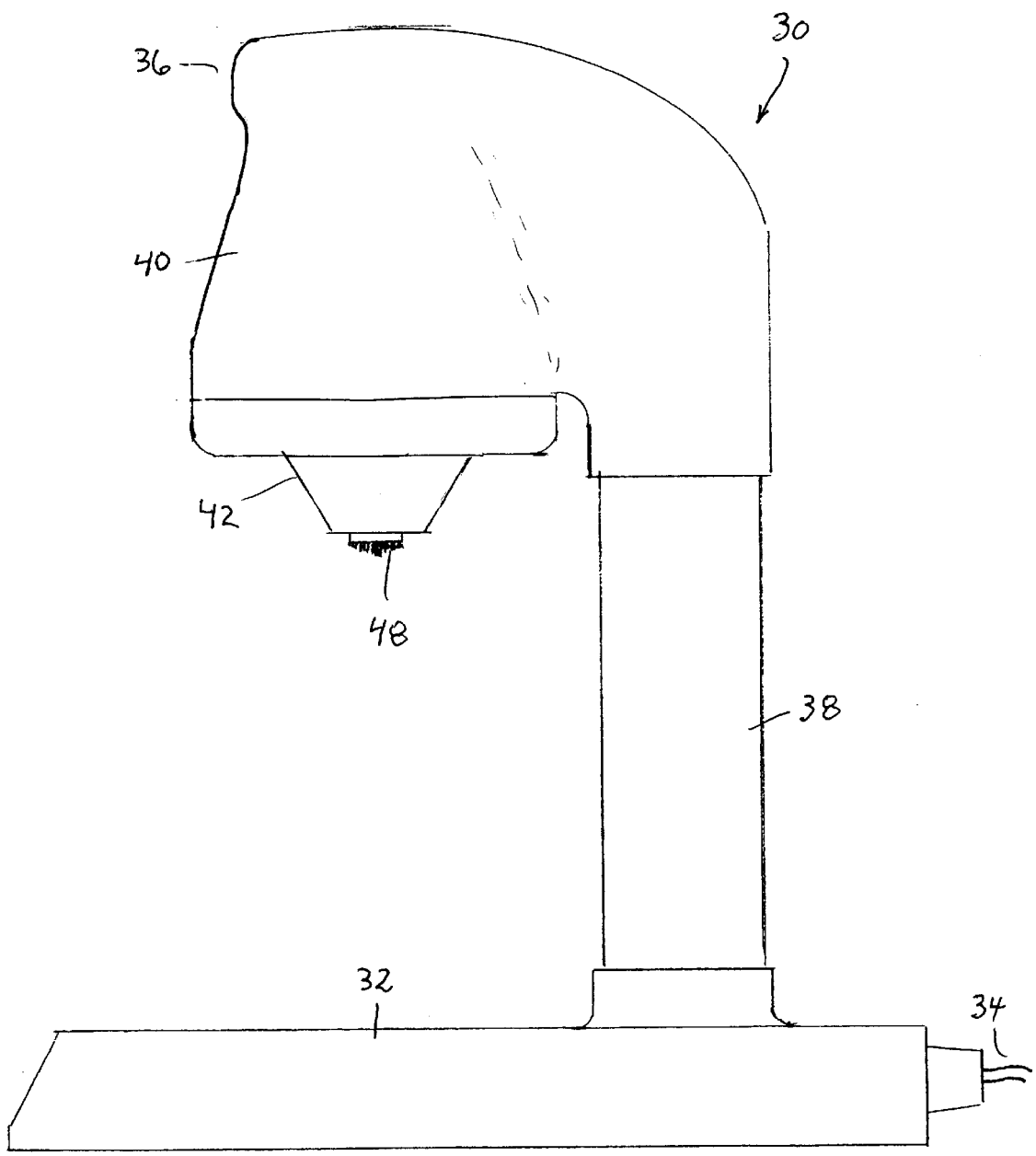
FIG. 3 is a side view of the invention.
Figure 4:
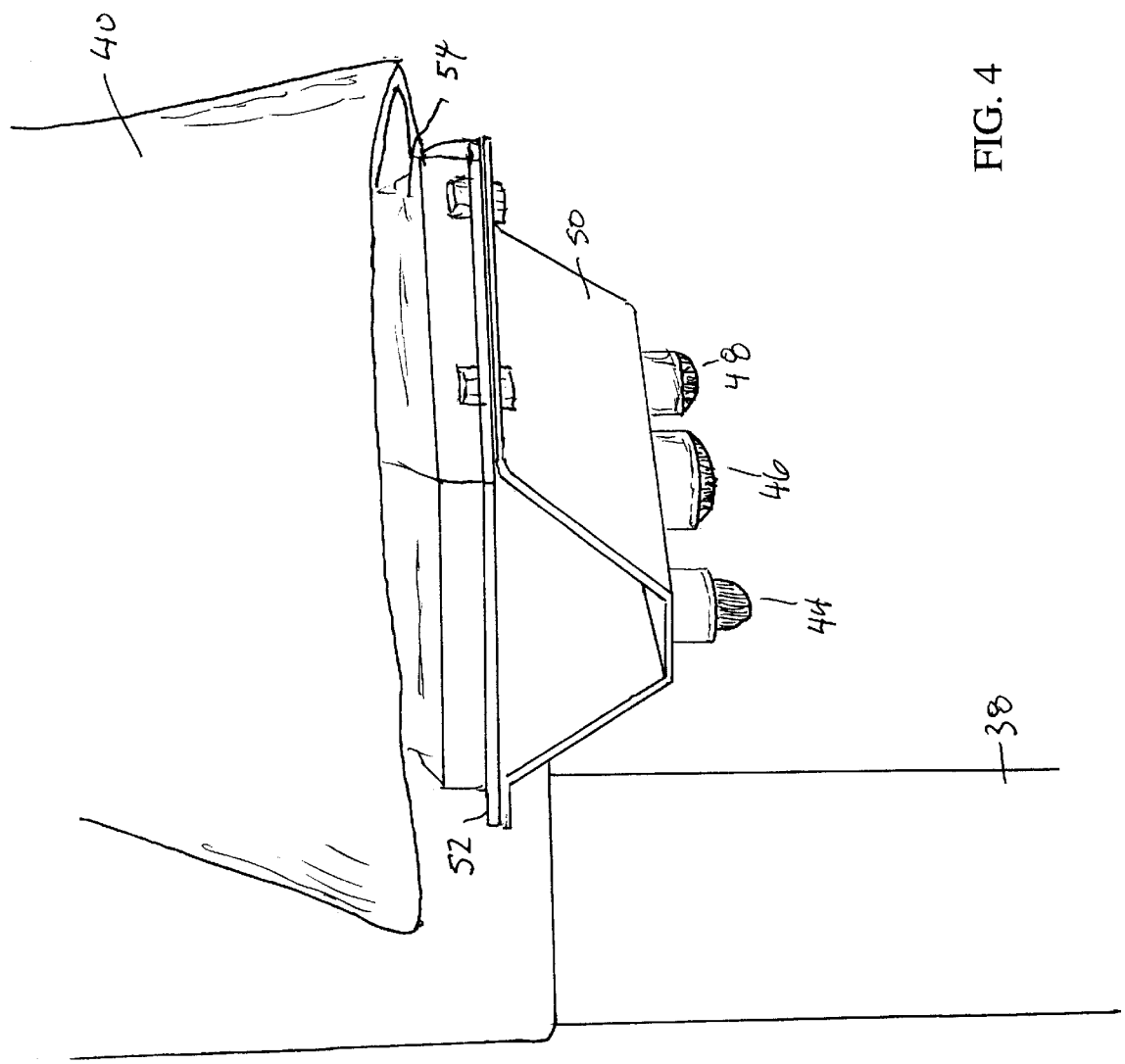
FIG. 4 is a detail of the polishing brushes of the invention with the brush housing removed for ease of illustration.
Figure 5:
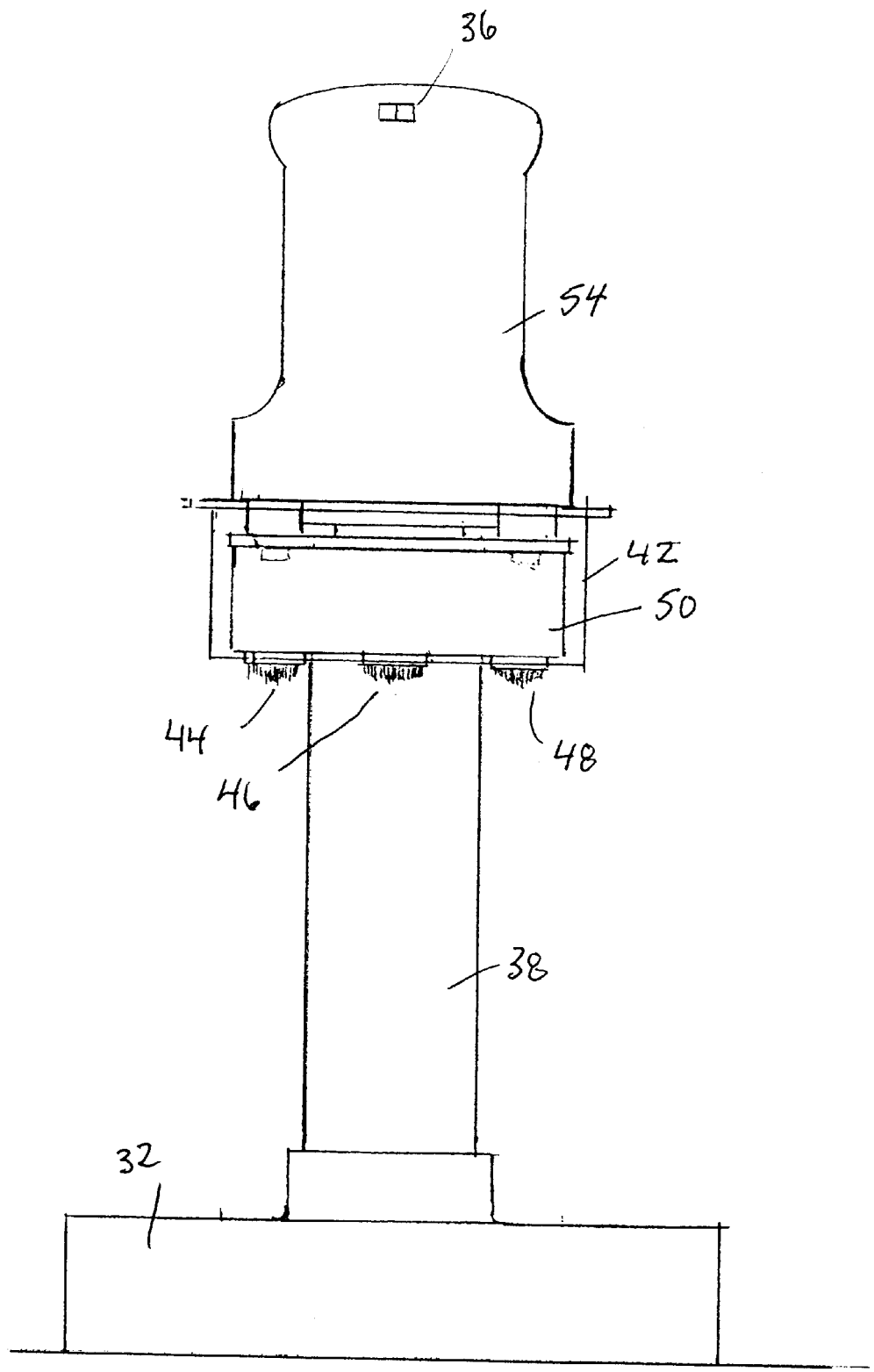
FIG. 5 is a view with the housing removed to better illustrate the orbital motor.

With reference to FIG. 1, a crown 10 is shown, which may be of a precious metal such as gold alloy, or porcelain or acrylic. It has a convoluted upper or functional surface 12 having a marginal ridge 14, buccal cusp 16, lingual cusp 18, triangle ridges 20, groove 22 and pit 24. These complex features of the functional surface are referred to as the anatomy.

The polishing device 30 of the invention is shown in FIG. 2 through 5. It has a base 32, source of electrical power 34, switch 36, vertical post 38, and machine housing 40. Attached to machine housing 40 is a brush housing 42. Extending downwardly from brush housing 42 is at least one, and preferably three or more brush heads 44, 46, 48. Brush heads 44, 46, 48 are formed of polishing brush filaments such as those used to form existing lathe polishing brushes. Each brush head has a different profile according to the different desired tasks. Preferably the heads of the brushes have curved, generally hemispherical, faces with different radii to allow polishing of different surfaces. Also, providing multiple brush heads allows the use of a different coarseness of polishing compound on each brush head, from coarse to fine.

Brushes 44, 46, 48 are mounted on brush plate 50 (FIG. 5) which extends downwardly from and is secured to plate 52 of orbital motor 54. Brush plate 50 extends down a sufficient depth so that a technician working at the device can see the surface of the workpiece. A suitable motor 54 is from a Makita Finishing Sander model BO4552K. The switch 36 turns the motor on and off without speed variability. A motor having a variable speed may also be used, although a variable speed is normally not required.

In operation, the technician having a gold crown to polish turns on the orbital motor 54 which imparts to brush heads 44, 46, 48 a rapid orbital motion, much as in an orbital sander. The technician then selects the brush with the appropriate radius and/or polishing compound and contacts the surface of the crown, thereby polishing it. Unlike the prior polishing devices, the anatomy of the crown is not thereby reduced.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A device for polishing a workpiece, said workpiece comprising a convoluted surface, said device comprising:
    a) a brush-supporting member;
    b) a motor for imparting an orbital motion to said brush-supporting member, said orbital motion being substantially within a plane of contact of said working surface of a polishing brush; and
    c) a polishing brush comprising a convex working surface mounted on said brush-supporting member;
    wherein said device is configured to permit a selected portion of said convoluted surface of said workpiece to be brought selectively into and out of said plane of contact of said working surface of said polishing brush.

2. The device of claim 1 wherein said brush-support member comprises a plate.

3. The device of claim 1 wherein said working surface comprises a generally hemispherical face.

4. The device of claim 3 wherein said generally hemispherical face faces downwardly from said housing.

5. The device of claim 1 further comprising a base for standing the device on a supporting surface.

6. The device of claim 1 comprising a plurality of brushes mounted on said brush-supporting member.

7. The device of claim 6 wherein said plurality of brushes comprises brushes having working surfaces of differing sizes or shapes.

8. The device of claim 1 wherein said convex working surface has a radius less than the transverse width of said workpiece.

9. The device of claim 1 wherein said workpiece is a dental appliance.

10. The device of claim 1 wherein said workpiece is a dental crown.

11. The device of claim 1 wherein said workpiece is a dental bridge.

12. The device of claim 1 wherein said workpiece is a piece of jewellery.

* * * * *